United States Patent [19]
Horn et al.

[11] Patent Number: 5,233,062
[45] Date of Patent: Aug. 3, 1993

[54] ANTIBIOTIC EICOSENOIC ACIDS

[75] Inventors: Wendy S. Horn, Westfield; Myra B. Kurtz, Martinsville; Jerrold M. Liesch, Princeton Junction; Jack L. Smith, Colonia, all of N.J.; Isabel Martin; Francisca Vicente, both of Madrid, Spain

[73] Assignee: Merck & Co., Inc., Rahway, N.J.

[21] Appl. No.: 851,594

[22] Filed: Mar. 16, 1992

[51] Int. Cl.$^5$ ............................................ C07C 101/00
[52] U.S. Cl. ...................... 554/109; 554/115; 554/219; 554/223; 554/213
[58] Field of Search ............... 554/103, 213, 219, 224, 554/115, 223; 514/558, 561, 560

[56] References Cited
U.S. PATENT DOCUMENTS

| | | | |
|---|---|---|---|
| 3,758,529 | 9/1973 | Craveri et al. | 260/404 |
| 3,928,572 | 12/1975 | Kluepfel et al. | 424/122 |
| 4,906,467 | 3/1990 | Schwartzman et al. | 424/80 |
| 5,019,593 | 5/1991 | Garrity et al. | 514/560 |

FOREIGN PATENT DOCUMENTS

301744A2 2/1989 European Pat. Off. .
410176A1 1/1991 European Pat. Off. .

*Primary Examiner*—José G. Dees
*Assistant Examiner*—Deborah D. Carr
*Attorney, Agent, or Firm*—Alice O. Robertson; Raymond M. Speer

[57] ABSTRACT

New antibiotic eicosenoic acids and a method of producing it are described. The acids have been found to have antifungal properties.

6 Claims, No Drawings

ANTIBIOTIC EICOSENOIC ACIDS

DESCRIPTION OF THE INVENTION

The present invention is directed to compounds represented by the formula

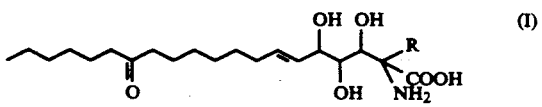

wherein R is $CH_2OH$ or $CH_3$.

When R above is $CH_2OH$, the compound is hereinafter referred to as Compound IA and may be identified by the following formula

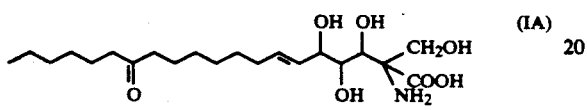

When R above is $CH_3$, the compound is hereinafter referred to as Compound IB and may be identified by the following formula

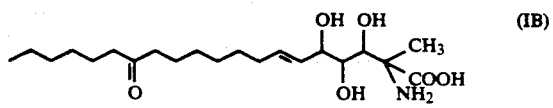

The structure of the compounds has been determined by detailed analysis of the spectral characteristics. The ultraviolet spectrum was obtained on a Beckman DV-70 spectrophotometer. The nuclear magnetic resonance (NMR) spectral data was obtained $CD_3OD$ on a Varian XL-300 NMR spectrometer. The heteronuclear multiple quantum coherence HMQC data was obtained on a Varian 500 NMR spectrometer. The mass spectral data was obtained on a Finnegan MAT 212 mass spectrometer at 90 eV electron impact-mass spectra (EI-MS) and MAT-90 fast atom bombardment mass spectra (FAB-MS).

COMPOUND IA

UV Spectrum

Compound IA was found to have a $\lambda_{max}$ (methanol)=205 nm ($\epsilon$=3254).

NMR Spectra

The $^1H$ and $^{13}C$ NMR data for Compound IA are as given below.

The specific shifts of the methine carbons bearing hydroxyls, the methylene and methyl groups were assigned using $^1H$-$^{13}C$ chemical shift correlation spectra (HETCOR) data. The hydroxymethyl group adjacent to C-1 was unambiguously assigned using HMQC data.

The characteristic $^1H$-NMR spectrum for IA is as follows: 0.9 t (J=6.7), 1.30 obsc. (10 H), 1.40 br., 1.55 br. (4H), 2.10 br, 2.45 t (4 H, J=7.3) 3.65 d (J=6.3), 3.85 d (J=10.7), 3.95 m, 4.10 t (J=7.3), 5.45 dd (J=15.6 and 7.3), 5.80 dt (J=15.6 and 6.9).

The characteristic $^{13}C$-NMR spectrum for IA is as follows: 214.63, 174.22, 135.66, 130.18, 76.21, 75.29, 71.84, 70.30, 64.95, 43.51, 43.49, 33.39, 32.78, 30.10, 30.17 (2 C), 29.98, 24.87, 24.89, 23.55, 14.33.

Mass Spectra

A molecular weight of 417 was determined by fast atom bombardment mass spectra (FAB-MS). A 417+$T_6$ ion was weakly apparent in electron impact (EI) with a strong ion for 399+$T_3$ (M-$H_2O$); the exact mass was measured as 399.2601 ($C_{21}H_{39}NO_6$=399.2620), leading to the assignment of $C_{21}H_{39}NO_7$ as the molecular formula.

The location of the ketone on C-14 was determined by derivatizing the carbonyl to the methoxime and silylating to obtain a base peak m/z 344 high resolution-mass spectra (HR-MS $C_{17}H_{32}NO_2$) and m/z 142 (HR-MS $C_8H_{16}NO$) confirming the expected position of the carbonyl. The O-methyloxime was prepared by adding an excess of methoxyamine hydrochloride to the substrate in methanol and leaving the solution at room temperature for 4 hours.

COMPOUND IB

UV Spectrum

Compound IB was found to have a $\lambda_{max}$ (methanol)=205 nm ($\epsilon$=4387).

NMR Spectra

The $^1H$ and $^{13}C$ NMR data for Compound IB are as follows:

The characteristic $^1H$-NMR spectrum for IB is as follows: 0.9 t (J=6.6), 1.29 br (10 H), 1.30 br., 1.40 s, 1.55 br., (4H), 2.05 br., 2.44 t (4 H, J=7.4), 3.69 d (J=7.4), 3.87 br., 4.11 t (J=7.4), 5.47 dd (J=15.2 and 7.6), 5.76 dt (J=15.2 and 6.6).

The characteristic $^{13}C$-NMR spectrum for IB is as follows: 214.63, 175.28, 135.67, 130.18, 76.23, 75.71, 72.45, 66.18, 43.48 (2 C), 33.45, 32.83, 30.04, 30.01, 30.16, 30.18, 25.56, 24.89, 24.87, 21.81, 14.38.

Mass Spectra

The molecular weight was determined to be 401 by FAB-MS and EI-MS. After derivatization with TMS, fragment ions indicated the aliphatic chain was identical to Compound IA. In the TMS derivative, an ion corresponding to the loss of water from the molecular ion was observed at m/z 599 (TMS derivative of 383). This compound corresponds to 383.2664 (calculated 383.2671) by HR-MS which indicated $C_{21}H_{39}NO_6$ as the molecular formula.

The compounds are light colored solids soluble in organic solvents such as methanol and DMSO. Thus, they are adaptable to be employed in solution or in aqueous dispersions.

The compounds of this invention have useful antifungal activities adapted to be employed for the control of various fungi, including those causing pathogenic mycotic infections. Compound IA is active against refractory pathogens such as *Candida albicans, Candida parapsilosis, Candida pseudotropicalis, Candida neoformans*. In view of substantial lack of toxicity against mammals, the coumpounds are useful in the treatment of fungal diseases. Compound IB is also active against a number of yeasts causing mycotic infections such as *Candida albicans, Cryptococous neoformans* and *Saccharomyces cerevisiae*. In addition Compound IA showed very strong antifungal activity against filamentous fungi such as *Ceratocystis ulmi* and *Alternaria solani*. The activity against filamentous fungi renders the compounds applicable for treatment of plants and soils against fungal infections and are further adaptable as preservatives and the compounds are useful in other antifungal applications, including treatment of plants and soil, or as sanitizing agents, or as preservatives in the paint, wood, textile, cosmetic, leather, fur, paper and pulp, plastics, fuel, rubber and food industries.

The antifungal compounds of the present invention may be produced by the cultivation of previously unknown strain of the microorganism *Paecilomyces variotii*, MF5537 in the culture collection of Merck and Co., Rahway, N.J. and recovering said compound from the culture broth. A sample of the culture capable of producing the compound has been deposited under the Budapest Treaty without restriction as to availability in the culture collection of the American Type Culture Collection at 12301 Park Drive, Rockville, Md., 20852. The culture has been assigned accession No. ATCC 74097.

The producing organism *Paecilomyces variotii* Bainier was isolated from the dung of a cottontail rabbit (*Sylvilagus floridanus*) collected in the Santa Catalina Mountains of Arizona. The morphological and cultural characteristics of the organism were observed on YpSs agar (a yeast potassium soluble starch agar from Difco Laboratories); V8 juice agar (200 ml V8 juice from Campbell Soup Co., 0.3% $CaCO_3$, 2.0% agar in distilled $H_2O$); and CYA, Czapek yeast autolysate agar, (yeast extract 0.5%, sucrose 3.0%, $K_2HPO_4$ 0.1%, $NaNO_3$ 0.03%, KCl 0.005%, $MgSO_4 \cdot 7H_2O$ 0.0005%, $FeSO_4 \cdot 7H_2O$ 0.0001%, 2.0% agar in distilled $H_2O$).

Colonies on YpSs, V8 juice, or CYA at 25° C., were slightly raised, densely velutinous to almost villose, with the margin minutely fimbriate, dull, dry, powdery in age, hyaline to white at the margin, soon developing a distinct pale yellow to yellow zone near the margin, becoming Straw Yellow (capitalized color names from Ridgway R.1912 Color Standards and Nomenclature, Washington, D.C.), Naples Yellow, Deep Colonial Buff, finally light olivaceous brown to olivaceous brown, Olive-Ocher, Isabella Color, Ecru-Olive, Old Gold, Buffy Citrine, or Citrine-Drab. Colonies were similar in reverse, with slight aromatic odor. Some sulcate medium buckling when colonies were grown at higher temperatures. Exudates absent.

Conidiophores arising from surface and aerial mycelium, 80–450 μm tall, determinate, macronematous to semi-macronematous, mononematous, with 1 to 5 tiers of sparsely to densely arranged branches, forming either verticillate or penicillate groups of metulae and phialides, thin-walled, with walls smooth, with finely granular cytoplasm. Conidiogenous cells discrete, enteroblastic, phialidic, 8–35×2–4 μm, 1–2 μm wide at conidiogenous locus, single or in dense clusters on metulae. Conidia ellipsoidal, broadly ellipsoidal, to subglobose, 6–4×2.5–4 μm, smooth, adhering in long chains, with chains tangled and widely divergent, joined by faint connectives, hyaline in KOH, light olivaceous brown in mass. Hyphae septate, branched, smooth or occasionally incrusted in age, up to 7 μm in diameter. Chlamydospores abundant in older mycelium arising directly from hyphae, pyriform to subglobose, smooth, with slightly thickened walls, 5–8 μm, in diameter, with refractive cytoplasm. Cleistothecia and sclerotia absent.

*Paecilomyces variotii* ATCC 74097 is distinguished from other species in the genus by a combination of olivaceous brown to yellowish brown colony colors, absence of cleistothecia, variable conidia shape ranging from subglobose to ellipsoidal, and thermotolerant growth. The thermotolerant nature of the strain is observed by its relatively robust growth at 37° C. and 45° C. as seen in the following table:

| Media | Temperature | | |
|---|---|---|---|
| | 25° C. | 37° C. | 45° C. |
| | Radial growth (mm) | | |
| YPSS | 29–30 | 46–48 | 25 |
| V8 Juice | 28–30 | 50–55 | 24–26 |
| CYA | 26–28 | 40 | 25–27 |

*Paecilomyces variotii* is not known to be a causal agent of systemic mycoses as are certain antibiotic producing fungi such as Aspergillus sp.

The compounds of the present invention are produced during the aerobic fermentation of suitable nutrient media under conditions described hereinafter with a producing strain of *Paecilomyces variotii* ATCC 74097.

Suitable nutrient media contain sources of carbon and nitrogen assimilable by the microorganism and generally low levels of inorganic salts. In addition, the fermentation media may contain traces of metal necessary for the growth of the microorganisms and production of the desired compound. These are usually present in sufficient concentrations in the complex sources of carbon and nitrogen, which may be used as nutrient sources, but can, of course, be added separately to the medium, if desired.

In general, nutrients such as dextrose, sucrose, maltose, glycerol, lactose, dextran, brown rice, cerelose, corn meal, millet, corn, oat flour, glutamic acid, and the like, are suitable sources of assimilable carbon in the nutrient media. The exact quantity of the carbon source which is utilized in the medium will depend, in part, upon the other ingredients in the medium, but it is usually found that an amount of carbohydrate between 0.5 and 90% by weight of the medium is satisfactory. These carbon sources can be used individually or several such carbon sources may be combined in the same medium.

Various nitrogen sources such as yeast hydrolysates, yeast autolysates, yeast cells, tomato paste, soybean meal, casein hydrolysates, yeast extracts, glutamic acid corn steep liquors, distillers solubles, cottonseed meal, meat extract, corn, millet and the like, are readily assimilable by *Paecilomyces variotii* MF537 ATCC 74097 in the production of the instant compounds. The various sources of nitrogen can be used alone or in combination in amounts ranging from 0.2 to 90% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and the like ions. Also included are trace metals such as cobalt, manganese, iron, molybdenum, zinc, cadmium, and the like.

The following solid medium is a preferred medium for growing strains of *Paecilomyces variotii*:

| Medium I (BRF) | |
|---|---|
| | (per 250 ml flask) |
| Brown rice | 10 g |
| Base liquid* | 20 ml |
| *Base liquid per liter | |

| | |
|---|---|
| | distilled water |
| Yeast extract | 1.0 g |
| Sodium tartrate | 0.5 g |
| KH$_2$PO$_4$ | 0.5 g |

Another medium found useful is the following:

| Medium II (F204) | |
|---|---|
| | (per 250 ml flask) |
| Millet | 15 g |
| Yeast extract | 0.5 g |
| Sodium tartrate | 0.1 g |
| Ferrous sulfate crystals | 0.01 g |
| Monosodium glutamic acid | 0.1 g |
| Corn oil | 0.1 ml |
| Distilled water | 15.0 ml |

For producing the compounds of the present invention, a fermentation medium is prepared by inoculating spores or mycelia into a suitable medium and cultivating under aerobic conditions.

The procedure generally is first to inoculate a 250-ml flask containing 54 milliliters of a nutrient seed medium with a preserved source such as an agar slant or a vial containing frozen vegetative mycelium and to obtain, preferably through a two step procedure, growth of the organisms which serve as seeds in the production of the antifungal agent.

In this process, a slant section of a preserved culture of MF 5537 ATCC 74097 is inoculated in an appropriate liquid nutrient seed medium. The preferred seed medium is one known as KF Seed Medium of the following composition:

| | |
|---|---|
| Corn Steep Liquor | 5 g |
| Tomato Paste | 40 g |
| Oat Flour | 10 g |
| Glucose | 10 g |
| Trace Elements Mix | 10 ml |
| Distilled Water | to 1000 ml |
| pH 6.8 | |
| Trace Elements Mix: | |
| FeSO$_4$.7H$_2$O | 1 g |
| MnSO$_4$.4H$_2$O | 1 g |
| CuCl$_2$.2H$_2$O | 25 mg |
| CaCl$_2$ | 100 mg |
| H$_3$BO$_3$ | 56 mg |
| (NH$_4$)$_6$MoO$_2$.H$_2$O | 19 mg |
| ZnSO$_4$.7H$_2$O | 200 mg |
| Distilled Water | to 1000 ml |

After inoculation, the flasks are incubated with or without agitation at temperatures in the range of from about 25° C. to about 30° C., usually about 28° C. Agitation when employed, may be up to 400 RPM, preferably, about 200 to 220 RPM. The incubation is carried out over a period of from 1 to 10 days. When growth is abundant, usually between 2 and 4 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 2 days. The growth then is employed to inoculate the production medium.

For production, a solid medium is preferred. The fermentation production medium, such as those previously described is inoculated with the culture growth, and incubated for 3 to 30 days, usually 7 to 14 days with or without agitation. The fermentation may be conducted at temperatures ranging from about 20° C. to about 40° C. For optimum results, it is most convenient to conduct these fermentations at a temperature in the range of from about 15° C. to about 30° C. Temperatures of about 25° C. are most preferred. The pH of the nutrient medium suitable for producing the instant compounds can vary the about 3.0 to 8.0 with a preferred range of from about 4.0 to 6.0. After the appropriate period for the production of the desired compound or compounds, the latter is recovered from the fermentation medium as hereinafter more fully described.

When the fermentation is to be on a small scale, it is conveniently carried out by placing suitable quantities of nutrient medium in a flask employing known sterile techniques, inoculating the flask with either spores or vegetative cellular growth of Paecilomyces variotii MF5533, loosely stoppering the flask with cotton and permitting the fermentation to proceed at a constant temperature of about 25° C. on a rotary shaker at from 0 to 300 RPM for about 2 to 21 days.

Recovery may be carried out by extracting the fermentation medium with a water-miscible solvent such as lower alcohols. The extract is placed on a non-ionic adsorbent column to adsorb the active component and to remove the water soluble impurities in the effluent. Thereafter, the adsorbed material is eluted from the column using alcohol such as methanol but preferably aqueous acetone and collecting the fractions. Fractions shown positive on the yeast KDS synthase inhibition assay are combined and concentrated under reduced pressure to obtain crude product or products where more than one positive fractions are noted.

The KDS synthase inhibition assay (also known as the serine palmitoyltransferase assay) which may be used to determine inhibition of the enzyme is similar to that described by R. D. Williams, et al., in Arch. Biochem. and Biophys. 228, 2282-291 (1984). Briefly, a 5 microliter test sample of the fermentation medium is added to an assay mixture (final volume of 100 microliters) consisting of 100 mM 4-(2-hydroxyethyl)-1-piperazineethansulfonic acid (HEPES) pH 8.5, 2.5 mM EDTA, 0.1 mM palmitoyl CoA, 0.1 mM pyridoxyl-5'phosphate, 0.1 mM $^3$H-serine, 0.1 mM dithiothreitol (DTT) and 50 micrograms of microsomal membranes prepared from Saccharomyces cerevisiae. After a 30 minute reaction at 30° C., 100 milliliters of ice cold trichloroacetic acid (TCA) is added and the sample precipitated for 15 minutes at 4°0 C. The precipitated $^3$H-ketodihydrosphingosine is separated from the unreacted $^3$H-serine by filtration onto a filter mat in a Skatron cell harvester and radioactivity is counted in an LKB Beta-Plate scintillation counter.

The antifungal activity of the compounds may be detected in an antifungal assay employing disc diffusion methods against a panel of representative yeasts, filamentous fungi (molds) and bacteria.

For carrying out the assay, seeded assay plates are prepared in the following manner according to the type of assay strain.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

Inocula for yeasts and Streptomyces strains are prepared from overnight broth cultures then diluted into potato dextrose agar to a final concentration of either 40 percent or 70 percent transmission at 660 nm.

For strains of *Candida albicans* and *Saccharomyces cerevisiae*, sterile saline is employed in place of potato dextrose broth. Assay plates are prepared by diluting the inoculum into appropriate molten agar medium, cooled to 45° C. to obtain a final concentration of 4 percent.

Seeded agar for *Bacillus subtilis* sp. is prepared from a commercially available spore suspension which is diluted directly into molten agar (45° C.) to obtain a final concentration of 0.1 percent.

The seeded agar media thus prepared are dispensed into Petri dishes for assays (11 milliliters per dish).

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to be seeded assay plates and the sample rewet with 25 percent sterile aqueous dimethysulfoxide (25 μl/disc). The assay plates are then incubated at either 28° C. or 37° C. for 24 hours.

Following incubation, the inhibition zones are measured and recorded. The measurements are made from the extreme edge where growth differs from the background zone. The zones are noted as to appearance as fuzzy edge and clear center, hazy throughout, slightly hazy, very hazy or ringed.

The product of the present invention demonstrated a broad spectrum of antimicrobial, especially antifungal activity in the foregoing tests. Particularly large inhibition zones were noted with, for example, *Alternaria solani, Ceratocytis ulmi, Fusarium oxysporum, Rhizomucor miehei, Candida albicans Cryptococcus laurentii, Candida tropicalis* and Streptomyces sp.

In view of the broad spectrum of activity, the products of the present invention either singly or as a mixture are adaptable to being utilized in various applications of antifungal compositions. In such use, compounds may be admixed with a biologically inert carrier, generally with aid of a surface active dispersing agent, the nature of which would vary depending on whether the use is for the control of pathogens infecting man or animals, or for control of fungi in agriculture such as in soil or plant parts, or for the control of fungi in or on articles.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the useful pharmaceutical media, including, for liquid preparations, liquid carriers such as water, glycols, oil, alcohols, and the like; for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert carrier which includes finely divided dry or liquid diluents, extenders, fillers, conditioners and excipients, including various clays, diatomaceous earth, talc, and the like, or water and various organic liquids such as a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of formula I.

The following examples illustrate the invention but are not to be construed as limiting:

EXAMPLE I

A. Fermentation

A 250-milliliter flask containing 54 milliliters of KF seed medium was inoculated with mycelia and spores of MF 5537 contained in a soil tube. This flask was incubated for 3 days with shaking at 28° C. The resulting culture was then mixed with an equal volume of 20 percent glycerol to make frozen vegative mycelia. The FVM were stored at −80° C. Secondary FVMs were prepared from a primary FVM grown in KF seed medium and similarly diluted with glyercol.

Primary seed cultures were prepared by inoculating a flask of KF seed medium with 2 milliliters of an FVM preparation of MF5537 and incubating for three days with shaking. The resulting primary seed culture was then used to inoculate secondary KF seed cultures (2 ml of the primary seed culture/54 ml portion of the secondary seed medium).

Two milliliters of the seed culture thus prepared were added to each of sixty 250 milliliter production flasks containing BRF medium which had been steam sterilized at 15 psi for 20 minutes, then moistened with 10 milliliters of distilled water and sterilized again. The production cultures were grown statically by incubating at 25° C. for 14 days.

At harvest, 40 milliliters of methanol then was added to each flask and the flasks shaken at 25° C. for 30 minutes at 220 rpm to extract the secondary metabolite into the methanol.

B. Isolation

The extracts from the sixty production flasks were pooled, vacuum filtered through CELITE (diatomaceous earth, Johns Manville). The culture solids retained on CELITE were combined and extracted overnite in one liter of methanol and then filtered through Celite. The filtered methanol extracts were combined, diluted to 20/80 methanol/water and absorbed on a 4 liter DIAION SP-207 (brominated styrene-divinylbenzene copolymer, Mitsubishi Chemical Industries). This was eluted successively with 40 percent aqueous acetone, 60 percent aqueous acetone and finally methanol. Compound IA and IB eluted with 60 percent acetone. Fractions which were active as determined by KDS synthase assay were concentrated by adsorption on a 75 milliliter DIAION SP-207 column and then eluted with methanol. The methanol elute was concentrated under vacuum, the concentrate reconstituted in 250 milliliters of 10/90 methanol/water, the pH adjusted to 4.4 and adsorbed on a 50 milliliter DOWEX 50 (H+) (cation exchange, Dow Chemical Co.) column. Compounds IA and IB were eluted with 0.2N aqueous pyridine. Compounds IA and IB were further purified by repeated semi-preparative HPLC using ODS-30 (octadecylsilyl reverse phase 25 cm×9.4 mm) column, eluting with 70/30 methanol/0.01M phosphate buffer (pH 7), monitored by UV at 205 nm. Fractions were analyzed by analytical HPLC using the conditions above described. Fractions containing Compound IA (retention time ~10 minutes) were pooled and desalted by adsorbing onto DIAION HP-20 (styrene-divinylbenzene copolymer, Mitsubishi) and eluting with methanol. Fractions containing Compound IB (RT~11 minutes) were similarly pooled and desalted on DIAION HP-20.

Compounds IA and IB had the spectra and other physical properties previously set forth.

EXAMPLE II

For oral administration tablets are convenient. 1000 compressed tablets each containing 500 milligrams of Compound IA are prepared from the following:

|  | grams |
|---|---|
| Compound I | 500 |
| Starch | 750 |
| Dibasic calcium phosphate, hydrous | 5000 |
| Calcium stearate | 2.5 |

The ingredients are finally powdered and mixed well and granulated with 10 percent starchpaste. The granulation is dried and compressed into tablets.

EXAMPLE III

The parenteral administration, injectable solutions may be prepared by conventional procedures having the following formulation:

| Dextrose | 12.5 grams |
|---|---|
| Water | 250 milliliters |
| Compound IB | 400 milligrams |

The ingredients are blended and thereafter sterilized for use.

EXAMPLE IV

An ointment suitable for topical application may be prepared by intimately dispersing 13 milligrams of Compound IA in 1 gram of commercially available polyethylene/hydrocarbon gel.

What is claimed is:

1. A compound having the formula

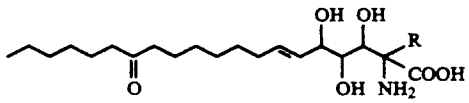

wherein R is $CH_2OH$ or $CH_3$.

2. A compound according to claim 1 wherein R is $CH_2OH$.

3. A compound according to claim 1 wherein R is $CH_3$.

4. An antifungal composition comprising the compound of claim 1 in admixture with a pharmaceutically acceptable carrier.

5. A method for inhibiting fungal growth comprising applying to the area where growth is to be controlled, an antifungally effective amount of the compound of claim 1.

6. A method for controlling mycotic infections comprising administering to a subject in need of therapy an antimycotic amount of the compound of claim 1.

* * * * *